US012760053B2

(12) United States Patent
Bonte et al.

(10) Patent No.: US 12,760,053 B2
(45) Date of Patent: Oct. 13, 2026

(54) PROCESS FOR THE PURIFICATION OF AN ACIDIC HUMAN MILK OLIGOSACCHARIDE FROM FERMENTATION BROTH

(71) Applicant: FrieslandCampina Nederland B.V., Amersfoort (NL)

(72) Inventors: Alfred Willy Bonte, Wageningen (NL); Franciscus Johannes Hubertus Jeurissen, Wageningen (NL); Martina Henrica Maria Van Genuchten, Wageningen (NL)

(73) Assignee: FrieslandCampina Nederland B.V., Amersfoort (NL)

( * ) Notice: Subject to any disclaimer, the term of this patent is extended or adjusted under 35 U.S.C. 154(b) by 775 days.

(21) Appl. No.: 18/032,933

(22) PCT Filed: Oct. 29, 2021

(86) PCT No.: PCT/EP2021/080094
§ 371 (c)(1),
(2) Date: Apr. 20, 2023

(87) PCT Pub. No.: WO2022/090450
PCT Pub. Date: May 5, 2022

(65) Prior Publication Data

US 2023/0391814 A1 Dec. 7, 2023

(30) Foreign Application Priority Data

Oct. 30, 2020 (EP) .................................... 20204812

(51) Int. Cl.

| | |
|---|---|
| ***C07H 1/08*** | (2006.01) |
| ***B01D 15/36*** | (2006.01) |
| ***B01D 61/02*** | (2006.01) |
| ***B01J 39/05*** | (2017.01) |
| ***B01J 41/07*** | (2017.01) |
| ***B01J 41/13*** | (2017.01) |
| ***C12P 19/04*** | (2006.01) |

(52) U.S. Cl.
CPC ............. *C07H 1/08* (2013.01); *B01D 15/362* (2013.01); *B01D 15/363* (2013.01); *B01D 61/029* (2022.08); *B01J 39/05* (2017.01); *B01J 41/07* (2017.01); *B01J 41/13* (2017.01); *C12P 19/04* (2013.01)

(58) Field of Classification Search
CPC ......................... B01D 15/1864; B01D 15/362; B01D 15/363; B01D 61/029; B01J 39/05; B01J 41/07; B01J 41/13; C07H 1/08; C12P 19/04
See application file for complete search history.

(56) References Cited

FOREIGN PATENT DOCUMENTS

| | | | | |
|---|---|---|---|---|
| EP | 3456836 | 3/2019 | | |
| EP | 3494807 | 6/2019 | | |
| WO | 2009113861 A2 | 9/2009 | | |
| WO | 2009113861 A3 | 11/2009 | | |
| WO | 2010106320 | 9/2010 | | |
| WO | 2017152918 | 9/2017 | | |
| WO | 2019043029 | 3/2019 | | |
| WO | WO-2019043029 A1 * | 3/2019 | ............. | A23L 33/30 |
| WO | 2019063757 | 4/2019 | | |
| WO | WO-2019101629 A1 * | 5/2019 | .............. | C12P 19/26 |
| WO | 2019229118 | 12/2019 | | |

OTHER PUBLICATIONS

International Search Report and Written Opinion, date of mailing Jan. 14, 2022; International Application No. PCT/EP2021/080094 (11 pgs.).

* cited by examiner

*Primary Examiner* — Patrick Orme
(74) *Attorney, Agent, or Firm* — Fitch, Even, Tabin & Flannery LLP

(57) ABSTRACT

The present invention relates to a process for the purification of an acidic human milk oligosaccharide (HMO) from a fermentation broth using ion exchange methods. This process allows for a reduction of the number and/or extent of desalting operations, such as electrodialysis. It is even possible to refrain from such operations.

19 Claims, No Drawings

PROCESS FOR THE PURIFICATION OF AN ACIDIC HUMAN MILK OLIGOSACCHARIDE FROM FERMENTATION BROTH

CROSS REFERENCE TO RELATED APPLICATIONS

This application is a U.S. national phase application of International Application No. PCT/EP2021/080094, filed Oct. 29, 2021, which claims benefit from Europe application No. 20204812.0, filed Oct. 30, 2020, which are each hereby incorporated herein by reference in their entirety.

FIELD

The invention relates to a process for the purification of a acidic human milk oligosaccharide (HMO).

BACKGROUND

Human milk contains various oligosaccharides (HMO's) which are important for a healthy development of infants. Many HMO's serve an important role in the development of a healthy intestinal microbiome.

Numerous HMO's exist; the most abundantly present in human milk are fucosylated lactoses such as 2'-fucosyllactose (2'-FL) and 3'-fucosyllactose (3'-FL), sialylated lactoses such as 3'-sialyllactose (3'-SL) and 6'-sialyllactose (6'-SL), and tetrasaccharides like lacto-N-tetraose (LNT) and lacto-N-neotetraose (LNnT).

2'-FL, 3-FL, LNT, and LNnT are neutral, in the sense that they are not charged. Neutral HMO's can be relatively easily purified from the fermentation broth in which they are produced. Anion- and cation-exchange chromatography are used in this purification for the removal of charged species.

For instance, WO 2019/063757 discloses a method for purifying fucosylated HMOs involving ultrafiltration of the fermentation broth, cation exchange using a strong cation exchange resin, anion exchange using a weak anion exchange resin in the $OH^-$ form, and finally adsorbing neutral components other than fucosylated HMO's using a highly porous weak cation exchange adsorbent resin.

Sialylated HMO's, such as 3'-sialyllactose (3'-SL) and 6'-silalyllactose (6'-SL), are acidic/negatively charged and are generally prepared in their sodium form. This negative charge hinders the application of the above-described purification technique for neutral HMO's, since the negatively charged HMO will compete with the other anions in binding to the anion exchange resin, resulting in poor separation.

WO 2009/113861 discloses isolation of sialylated oligosaccharides from a defatted, preferably protein-free milk stream by subjecting said milk stream—after an optional softening and nanofiltration procedure—to (i) a cation exchange step, (ii) an anion exchange step using an anion exchange resin in the free base form and having a moisture content of 30-48%, (iii) binding the oligosaccharides to a microporous or gel-type anion exchange resin with a moisture content of >45% and preferably also in the free base form, and (iv) eluting the oligosaccharides from said resin using an acid salt solution.

WO 2010/106320 discloses a process for the isolation and purification of 3'-SL from whey by demineralizing the whey using a series of two anion exchange resins and two cation exchange resins, followed by contacting the demineralized whey with a strong acidic cation exchange resin and a weakly basic anion resin. The 3'-SL binds to the weak anion exchange resin and is subsequently eluted therefrom.

WO 2017/152918 discloses a process for isolating sialylated oligosaccharides from a fermentation broth by (i) ultrafiltration, (ii) nanofiltration, (iii) an optional activated charcoal treatment and (iv) a treatment with a strong anion or a strong cation exchange resin. Negatively charged materials, including the sialylated oligosaccharides, bind to the strong anion exchange resin. In one embodiment, the sialylated oligosaccharides are recovered from the anion exchange resin by elution with an aqueous acid or salt solution. In another embodiment, the product is eluted from a strong cation exchange resin in the $H^+$ form and is subsequently neutralized with NaOH, thereby resulting in the sodium salt of the oligosaccharide.

WO 2019/229118 discloses the purification of sialyllactose from other carbohydrates in a fermentation broth by removing cell mass using at least one but preferably two ultrafiltration steps, treating the resulting solution with a cation exchange resin in the $H^+$ form and a strong anion exchange resin in the $Cl^-$ form, and removing carbohydrates from the resulting solution by filtration over two membranes: one with a molecular weight cut-off of 300-500 Da and one with a molecular weight cut-off of 600-800 Da. After treatment with the cation exchange resin, the solution was neutralized with NaOH to pH 7. After treatment with the anion exchange resin, the solution was again neutralized to pH 7. Hence, a lot of salt was introduced, which then had to be removed by electrodialysis.

WO 2019/043029 discloses the purification of sialyllactose from other carbohydrates in a fermentation broth by separating biomass from the fermentation broth by centrifugation, microfiltration or ultrafiltration, removing cations using a strong cation exchange resin in the $H^+$ form, raising the pH of the resulting sialyllactose-containing elute to 7, removing anionic impurities using a strong anion exchange resin in the $Cl^-$ form, and removing compounds with a molecular weight lower than that of the slalyllactose by nanofiltration or diafiltration.

Also this process involves neutralization of sialyllactose with NaOH to pH 7 between the two ion exchange treatments, resulting in a lot of salt which had to be removed.

EP 3 456 836 A1 discloses two processes for the separation of sialyllactose from a fermentation broth. Both processes involve ion exchange steps, followed by ultrafiltration, nanofiltration, and/or activated charcoal treatment. According to the first process, the ion exchange steps start with an anion exchange using a strong anion exchange resin in $Cl^-$ form, which is followed by a cation exchange step using a cation exchange resin in the $H^+$ or $Na^+$ form. A disclosed advantage of this embodiment is that no neutralization is required in between these two ion exchange steps.

A disadvantage of this embodiment, however, is that the anion exchange step may raise the pH of the solution, which may cause any salts (like Ca-salts) to precipitate. It is therefore more desired to start with cation instead of anion exchange in order to remove the metal ions before they can precipitate.

The second process starts with cation exchange using a resin in the $H^+$ or $Na^+$ form, followed by anion exchange using a strong anion exchange resin in $Cl^-$ form. If a cation exchange resin in the $H^+$ form is used, neutralization with NaOH to form the sodium salt of sialyllactose is required before submission to the strong anion exchange resin. Otherwise, the sialyllactose will bind to the strong anion exchange resin. This neutralization requires the introduction of salts.

DETAILED DESCRIPTION

It has now been found that it is possible to isolate and purify acidic HMO's to a satisfactory extent from a fermentation broth using ion exchange methods, by introducing less salt and/or without neutralization steps in between ion exchange steps. As a result, the number and/or extent of desalting operations, such as electrodialysis, can be reduced. It is even possible to refrain from such operations.

The present invention therefore relates to a process for the purification of an acidic human milk oligosaccharide (HMO) from a fermentation broth, the process comprising the steps of:

(i) separating biomass from the fermentation broth to provide a crude solution;

(ii) subjecting the crude solution to cation exchange using a cation exchange material in the $H^+$ form, thereby obtaining a solution with a pH in the range 1-3;

(iii) subjecting the solution with a pH in the range 1-3 to anion exchange using a weakly basic anion exchange material in the $Cl^-$ form, thereby obtaining a solution with a pH in the range 1.5-5.5, preferably 1.5-4;

(iv) subjecting the solution with pH in the range 1.5-5.5, preferably 1.5-4, to adsorption using an adsorbent material in order to remove neutral organic compounds;

(v) optionally adjusting the pH of the solution having been subjected to adsorption to a value in the range 5-6;

(vi) optionally subjecting the solution to anion exchange using an anion exchange resin, thereby binding the acidic human milk oligosaccharide to the resin followed by eluting the acidic human milk oligosaccharide from the resin using a salt solution, this optional step being conducted between steps (iii) and (iv) or steps (iv) and (v);

thereby obtaining a purified solution comprising said acidic human milk oligosaccharide.

Examples of acidic human milk oligosaccharides that can be purified with this process include sialylated oligosaccharides, preferably selected from the group consisting of 6'-sialyllactose (6'-SL), 3'-sialyllactose (3'-SL), disialyllacto-N-tetraose, 3'-sialyl-3-fucosyllactose, sialyllacto-N-tetraose, fucosyl sialyl lacto-N-neohexaose, di-fucosyl sialyllacto-N-hexaose, sialyllacto-N-tetraose a, sialyllacto-N-tetraose b, fucosyl sialyllacto-N-hexaose, and 3'-fucosyl sialyllacto-N-tetraose. More preferred HMOs to be purified by this process are 6'-sialyllactose (6'-SL), 3'-sialyllactose (3'-SL), disialyllacto-N-tetraose, 3'-sialyl-3-fucosyllactose, and sialyllacto-N-tetraose. Most preferably, the process of this invention is used to purify 6'-sialyllactose (6'-SL) or 3'-sialyllactose (3'-SL).

During treatment with the ion exchange materials in steps (ii) and (iii), the acidic HMO stays in solution while other charged components are effectively removed. The acidic HMO will not—or only to a minor extent—bind to the weakly basic anion exchange material used in step (iii).

It is theorized that due to the low pH conditions of the solution when being subjected to the weakly basic anion exchange resin in step (iii), the HMO becomes protonated and thereby behaves as a neutral HMO. Other negatively charged components in the solution, on the other hand, will bind to the weakly basic anion exchange material and hence be removed from the solution.

A fermentation broth typically comprises a micro-organism or remains thereof, used for the production of the HMO, and nutrients for the micro-organisms. Residual carbon sources from which the HMO is produced can also be present. Further, one or more side-products produced by the micro-organism may be present.

The fermentative production of the HMO can be carried out based on known methodology for the microbiological production of oligosaccharides, e.g. as described in the prior art mentioned above or the prior art cited therein. Lactose is preferably used as a carbon source that is converted into HMO by the micro-organism in the fermentation broth.

Separation of biomass (step (i)) from the liquid phase can be accomplished in a manner known per se for the type of fermentation broth that has been used to produce the HMO in. Use can be made of clarification and/or filtration. Prior or during step (i) the broth can be subjected to a degassing step. Suitable degassing steps are generally known in the art. Degassing is advantageous in that it reduces the risk of the formation of gas bubbles during subsequent steps. Such gas bubbles could detrimentally affect the flow of the solution through packed columns and in case loose beads are used, gas formation could cause floating of the adsorbent or ion exchange material.

The crude solution obtained by separation step (i) may be subjected to microfiltration (MF) and/or ultrafiltration (UF). MF is usually carried out with a membrane having a pore size of less than 1 μm, preferably of about 0.1-0.2 μm. The MF is particularly suitable to remove cell material (complete cells, fragments thereof) and other supramolecular debris. MF can be performed at about ambient temperature. Usually the temperature is in the range of 20-75° C. Preferably, the MF is carried out at a temperature of at least 30° C., more preferably at a temperature in the range of 35-70° C. A relatively high temperature has been found advantageous for an increased yield of the HMO. Particularly advantageous is a temperature in the range of about 40-50° C., such as a temperature of about 45° C., or a temperature in the range of about 60-70° C., such as about 65° C. Without being bound by theory, the inventors consider that excretion from the biomass into the liquid phase is improved at elevated temperature. Further, a high temperature, in particular a temperature of about 60° C. to 70° C. is advantageous for achieving a higher concentration factor of cell material during microfiltration, which has a positive effect on the yield of the HMO.

The ultrafiltration step is particularly suitable to remove proteins, DNA and/or endotoxins from the permeate. Heat treatment serves to modify protein, e.g. denature it, whereby it becomes less permeable through the UF membrane. The UF membrane preferably has a cut-off of 5 kDa or less, in particular about 3 kDa or less. The cut-off usually is at least about 1 kDa.

In a preferred embodiment, the MF permeate, before being subjected to ultrafiltration, is cooled to a temperature below 20° C., more preferably below 15° C., most preferably in the range 8-12° C.

In order to increase HMO recovery from the broth, the MF and/or the UF may be applied with diafiltration.

The crude solution, after the optional filtration steps discussed above, is then treated with a cation exchange material (step (ii)); a weakly basic anion exchange material (step (iii)); and an adsorbent material (step (iv)).

The terms 'weak' ion exchange and 'strong' ion exchange' are generally known in the art. A strong ion exchanger will not significantly loose the charge on its matrix once the ion exchanger is equilibrated, and so a wide pH range—generally from strongly acidic pH to a strongly alkaline pH—can be used. Strong anion exchange resins are generally characterized by the presence of quaternary ammonium groups.

Weak ion exchangers have a more specific range of pH values in which they will maintain their charge, usually an acidic to about neutral pH in the case of weak anion exchange materials and an alkaline to about neutral pH in the case of weak cation exchange materials. Weak anion exchange groups are generally characterized by the absence of quaternary ammonium groups. Common weak anion exchange groups are tertiary amine groups.

Ion exchange materials can be provided in packed columns, as membranes, as charge-modified depth filter cartridges, or used as a suspended or fluidized material.

Ion exchange materials typically comprise a matrix provided with fixed functional groups (cationic for anion exchange materials, anionic for cation exchange materials). Examples of suitable matrices are fibrous gels, microcrystalline gels, or beaded gels. These may be made of, for instance, polysaccharide based materials (e.g. agaroses, sepharoses, celluloses), silica-based materials, or organic (co) polymers (e.g. polyacrylamides, polystyrenes). The functional groups can be introduced by derivatization.

The ion exchange materials can be employed in a manner known per se, e.g. as specified by the supplier, for a specific material of interest. An advantage of strong ion exchangers is that they can capture ions at a wide pH range. An advantage of weak ion exchangers is their easy regeneration: less chemicals are needed for regeneration. The ion exchange materials used in the process of the present invention should satisfy food grade standards—i.e. being allowed to use for producing food ingredients—and preferably also satisfy various religious food standards (e.g. halal and kosher).

The cation-exchange material in step (ii) is used as a cation exchanger, i.e. for the removal of positively charged components. The cation-exchange step (ii) preferably comprises treatment with a strong cation-exchange material. Preferably, the cation-exchange material is a strong acid cation exchange material selected from the group consisting of styrene-divinylbenzene cation exchange resins, more preferably gel-type styrene-divinylbenzene cation exchange resins. The cation-exchange (step (ii)) is carried out using a cation-exchange material in the $H^+$ form. In a preferred embodiment, the cation-exchange material comprises sulfonic acid functional groups. Most preferably, the cation-exchange material is a strong acid cation exchange resin having a styrene/divinylbenzene gel-type matrix and sulfonic acid functional groups.

After treatment with the cation exchange material, the HMO-containing solution will have a pH in the range 1-3. This solution is subsequently subjected to an anion exchange material (step (iii)), without any need for raising the pH and introducing additional ions in the solution. As mentioned above, it is due to the low pH conditions during anion exchange that the HMO is protonated and thereby behaves as a neutral HMO.

The weakly basic anion-exchange material in step (iii) is used as an anion exchanger for the removal of negatively charged components, more in particular polyvalent ions such as phosphates and sulphates. The anion-exchange material is in the $Cl^-$ form, meaning that the anion exchange material contains $Cl^-$ counter ions, optionally in combination with other, e.g. $OH^-$, anions. Preferably, at least 90% of the anions are $Cl^-$ anions. It is also possible to use two anion exchange materials, one in the $Cl^-$ form and one in another, e.g. $OH^-$, form. During treatment of the filtered solution with this material, strong anions in the solution will bind to the material, whereas the majority of the acidic HMOs remains in solution.

The anion-exchange material is a weakly basic anion exchange material, preferably selected from the group consisting of styrene-divinylbenzene anion exchange resins and crosslinked acrylic anion exchange resins, more preferably gel-type styrene-divinylbenzene anion exchange resins and gel-type crosslinked acrylic anion exchange resins. The resin preferably has tertiary amine functional groups, more preferably dimethylamine functional groups. The anion exchange material is in the $Cl^-$ form. Whereas strong anion exchange resins would capture the protonated HMO in favour of organic acid impurities, a weak anion exchange resin preferentially captures anionic impurities while the protonated HMO flows through the column.

Regeneration of the anion exchange resin can be performed by HCl, which may subsequently be used as a regenerant for the cation exchange resin.

After the anion exchange treatment, the HMO-containing solution has a pH in the range 1.5-5.5, preferably 1.5-4. There is no need to raise or reduce the pH before subjecting the solution to the adsorbent material of step (iv). What is more, if the pH would be raised at this stage, organic acid impurities—that may still be present in the solution—will become negatively charged and will compete with the negatively charged HMO on the anion exchange material of optional step (vi).

The adsorbent material in step (iv) serves to remove non-ionic organic components and undissociated molecules and can be a conventional adsorbent material such as activated carbon, but preferably is a cation-exchange type of material. This cation exchange material preferably has a higher porosity and a lower density of ionic groups than the cation exchange material used in step (ii).

The porosity of the cation exchange material that can be used in step (iv) is preferably in the range 0.8 to 1.2 ml/g, more preferably 0.9 to 1.1 ml/g, and most preferably 0.95 to 1.05 ml/g. The BET surface area is preferably ≥600 $m^2/g$, more preferably ≥650 $m^2/g$, even more preferably ≥670 $m^2/g$ and most preferably ≥700 $m^2/g$.

The adsorbent material preferably is a styrene/divinyl benzene copolymer matrix of which the hydrophilicity is increased by the presence of sulphonic acid groups. In the process of the present invention it is used to adsorb components, typically organic components, in particular non-cationic components, more in particular components that are neutral at the pH of the solution. An advantage of such material over adsorbent materials like activated carbon is its inertness towards adsorption of acidic oligosaccharides. Surprisingly, the adsorbent material has been found suitable to also remove colour from the solution containing HMO. In particular it has been found effective in removing Maillard reaction products and aldol reaction products. The adsorbent material of step (iv)—which is preferably used after the cation-exchange (step (ii)) and the anion-exchange (step (iii)) steps—is also capable of removing (residual) cations. The adsorbent material in step (iv) is thus used for removal (via adsorption) of components, in particular neutral components.

Between steps (iii) and (iv) or after step (iv) and (v), the acidic solution is optionally subjected to a further anion exchange using an anion exchange resin, thereby binding the acidic human milk oligosaccharide to the resin.

In order to be able to bind the HMO, the anions on said anion exchange resin should have the right pKa. That is: the pKa of acid corresponding to said anions should be above the pKa of the acid form of the HMO to be purified. For instance, the pH of most sialyllactoses ranges up to about 2.9. The anionic exchange resin therefore preferably comprises anions of which the corresponding acids have a pKa above this value, more preferably above 4, and most preferably above 4.5.

Examples of suitable anions are hydroxyl ($OH^-$), bicarbonate ($HCO_3^-$) and monovalent organic acid anions such as acetate. In a most preferred embodiment, the anion is $OH^-$ The anion-exchange resin preferably is a weakly basic anion exchange material, since weak anion exchange resins generally have a higher number of functional groups than strong anion exchange resins and are therefore able to bind more HMO. The weak anion exchange resin is preferably selected from the group consisting of styrene-divinylbenzene anion exchange resins and crosslinked acrylic anion exchange resins, more preferably gel-type styrene-divinylbenzene anion exchange resins and microporous or gel-type crosslinked acrylic anion exchange resins. The resin preferably has tertiary amine functional groups, more preferably dimethylamine functional groups.

This is followed by eluting the acidic human milk oligosaccharide from said resin with a salt solution, preferably a NaCl solution.

Following the above steps (i)-(iv)—optionally including step (vi) between steps (iii) and (iv) or after step (iv)—the pH of the resulting solution may be adjusted to a value above 5, preferably in the range 5-6. This serves to reduce and/or prevent hydrolysis of the HMO. Preferably, KOH or NaOH, most preferably NaOH is used to raise the pH. This pH adjustment is particularly preferred when step (vi) has not been conducted.

It is usually sufficient to subject the crude solution to a single treatment sequence of strong cation-exchange, weak anion-exchange, adsorption, and optionally anion exchange and elution. However, if desired, the purified solution may be further treated, e.g. further purified and/or concentrated. Such further treatment preferably comprises nanofiltration (NF) and/or reverse osmosis (RO), optionally combined with diafiltration. NF or RO treatment is typically used to remove water, thereby concentrating the HMO. If a high flux is desired (requiring less membrane area), NF is considered to be particularly suitable. RO, which is operated at a relatively high pressure, has been found particularly suitable for obtaining a highly concentrated syrup with a high HMO content, such as a HMO content of 35-50 wt. %.

Alternatively or in addition, the purified solution may be subjected to an evaporation step in order to concentrate the solution, thereby producing a concentrated solution (a syrup).

In a specific embodiment, the concentration step (e.g. by NF, RO or evaporation), is followed by a sterilizing grade microfiltration step in order to ensure that no germs or spores are present in the solution.

The syrup preferably has an HMO content of at least 25 wt %, preferably 25-50 wt %, in particular of 25-35 wt %.

If desired, the HMO obtained by the process of the present invention can be subjected to a polishing step using an adsorbent material, such as activated carbon or a charge-modified depth filter. If the purified solution is to be subjected to a concentration step, the polishing step is usually carried out before the concentration step. The polishing step is particularly useful for the further reduction or removal of organic compounds, such as residual DNA fragments and/or to residual color.

The solution or syrup resulting from the process of the present invention may be subjected to a crystallisation step in order to obtain a crystalline HMO. Suitable crystallisation conditions can be based on those known in the art for oligosaccharides in general, or the HMO of interest in particular.

Alternatively, the solution or syrup may be subjected to a drying step in order to obtain HMO in powder form. Suitable drying conditions can be based on those known in the art for oligosaccharides in general, or the HMO of interest in particular. Preferred drying steps include spray-cooling, spray drying and lyophilisation (freeze-drying). Particularly good results have been achieved with spray-drying. The water content of the HMO powder is preferably less than 10 wt. %, more preferably less than 8 wt. %, even more preferably less than 5 wt. %. Most preferably, the water content of such powder is in the range of 2 to 4%, based on dry matter (DM).

The process of the present invention allows to achieve an HMO yield of 70% or more (based on HMO content in the fermentation broth) and a HMO purity of 90 wt. % or more (based on dry matter). In a preferred embodiment, the yield is in the range of 75-99 wt. %, in a specific embodiment in the range of 80-97 wt. % (based on HMO content in the fermentation broth).

Preferably, 6'-SL is obtained from the fermentation broth with a yield of 70% or more, more preferably 75% or more, even more preferably 80% or more, yet even more preferably 85% or more and most preferably 90% or more, all based on 6'-SL content in the fermentation broth.

EXAMPLE

A fermentation broth (20 kg) containing more than 15 g/l 3'-SL was microfiltrated in order to remove the bacterial biomass from the liquid. The MF permeate was cross-flow ultrafiltrated with a 5 kDa cut-off ceramic UF membrane (Tami Industries) in order to remove protein and remaining DNA.

The UF permeate was then further purified by ion exchange chromatography. In the first column, cations were removed on a strong cation exchange resin (styrene-divinyl benzene gel matrix with sulfonate functional groups) in the $H^+$ form. The solution leaving the column had a pH of 1.7-1.9. In the second chromatographic column, the solution was treated with a weakly basic anion exchange resin (crosslinked acrylic gel matrix with tertiary amines functional groups) in $Cl^-$ form, thereby exchanging anions with $Cl^-$ while keeping the pH between 1.7 and 1.9. The 3'-SL was not bound to the resin under these conditions. A third chromatographic purification step was conducted with adsorber resin in order to remove colorants and other adsorbing impurities, thereby not changing the pH of the solution. The adsorber resin was a styrene divinylbenzene copolymer matrix with sulphonic functional groups in the $H^+$ form, having a porosity of about 1.0 ml/g, an average pore size of 600-900 Ånstroms, and a surface area ≥700 $m^2/g$.

The purification effect of the ion exchange treatment is shown by the following analytical results (all amounts in % on dry matter; "n.d." stands for "not detected" and means that the concentration was below the detection limit of the respective analytical method).

| Component | before IEX | after AEX | after adsorber |
|---|---|---|---|
| 3'-SL | 67.79 | 80.26 | 80.42 |
| Phosphorus | 1.20 | n.d. | n.d. |
| Sulphate (inorganic) | 0.66 | n.d. | n.d. |

-continued

| Component | before IEX | after AEX | after adsorber |
|---|---|---|---|
| Chloride | n.d. | 2.63 | 2.10 |
| Sodium | 0.67 | n.d. | 0.42 |
| Potassium | 3.37 | n.d. | n.d. |
| Calcium | 0.06 | n.d. | n.d. |
| Magnesium | 0.23 | n.d. | n.d. |

After the chromatography steps, the pH of the solution could be increased to the desired level e.g. by the addition of sodium hydroxide. Still remaining substances such as chloride, organic acids, and small sugars can be further removed by means of crossflow nanofiltration, e.g. by using polymeric polypiperazine or polyamid membranes with a molecular weight cut-off between 150 and 500 Da. By doing so, a 3'-SL purity of 88% on dry matter and significantly higher can be reached.

The invention claimed is:

1. A process for the purification of an acidic human milk oligosaccharide (HMO) from a fermentation broth, the process comprising:

(i) separating biomass from the fermentation broth to provide a crude solution;

(ii) subjecting the crude solution to cation exchange using a cation exchange material in the $H^+$ form, thereby obtaining a solution with a pH in the range 1-3;

(iii) subjecting the solution with pH in the range 1-3 to anion exchange using a weakly basic anion exchange material in the $Cl^-$ form, thereby obtaining a solution with a pH in the range 1.5-5.5;

(iv) subjecting the solution with pH in the range 1.5-5.5 to adsorption using an adsorbent material in order to remove neutral organic compounds;

(v) optionally adjusting the pH of the solution having been subjected to adsorption to a value in the range 5-6;

(vi) optionally subjecting the solution to anion exchange using an anion exchange resin, thereby binding the acidic human milk oligosaccharide to the resin followed by eluting the acidic human milk oligosaccharide from the resin using a salt solution, this optional step being conducted between steps (iii) and (iv) or steps (iv) and (v);

thereby obtaining a purified solution comprising said acidic human milk oligosaccharide.

2. The process according to claim 1, wherein the acidic human milk oligosaccharide is selected from the group consisting of 6'-sialyllactose (6'-SL), 3'-sialyllactose (3'-SL), disialyllacto-N-tetraose, 3'-sialyl-3-fucosyllactose, and sialyllacto-N-tetraose.

3. The process according to claim 1, wherein the cation exchange material in step (ii) is a strong acid cation exchange material.

4. The process according to claim 1, wherein the weakly basic anion exchange material in step (iii) is selected from the group consisting of acrylic gel-type and styrene/divinylbenzene gel-type matrices with tertiary amine.

5. The process according to claim 1, wherein the adsorbent material in step (iv) is a weak cation exchange material.

6. The process according to claim 1, comprising subjecting the solution to anion exchange using an anion exchange resin, thereby binding the acidic human milk oligosaccharide to the resin followed by eluting the acidic human milk oligosaccharide from the resin using a salt solution, this step being conducted between steps (iii) and (iv) or steps (iv) and (v), and wherein the anion exchange resin is a weakly basic anion exchange resin.

7. The process according to claim 1, wherein step (i) includes the use of a membrane having a molecular weight cut-off of 5 kDa or less.

8. The process according to claim 1, wherein step (i) includes a microfiltration step which is performed at a temperature in the range of 20-75° C.

9. The process according to claim 8, wherein the microfiltration step forms a microfiltration (MF) permeate and the MF permeate is subjected to a cooling step before step (ii).

10. The process according to claim 1, comprising subjecting the solution to anion exchange using an anion exchange resin, thereby binding the acidic human milk oligosaccharide to the resin followed by eluting the acidic human milk oligosaccharide from the resin using a salt solution, this step being conducted between steps (iii) and (iv) or steps (iv) and (v), and wherein the anion exchange resin is in the $OH^-$ form.

11. The process according to claim 1, wherein the process further comprises subjecting the purified solution to nanofiltration and/or reverse osmosis.

12. The process according to claim 1, wherein the purified solution is, optionally after one or more further treatment steps, subjected to a drying or crystallisation step.

13. The process according to claim 12, wherein the human milk oligosaccharide is obtained in the form of a powder having a water content of less than 10 wt %.

14. The process according to claim 1, wherein the acidic human milk oligosaccharide is obtained in the form of a syrup.

15. A method for producing an acidic human milk oligosaccharide, the method comprising: producing an acidic human milk oligosaccharide by microbial fermentation in a fermentation broth and purifying the produced acidic human milk oligosaccharide using the process according to claim 1.

16. The process according to claim 1, comprising adjusting the pH of the solution having been subjected to adsorption to a value in the range 5-6.

17. The process according to claim 16, subjecting the solution to anion exchange using an anion exchange resin, thereby binding the acidic human milk oligosaccharide to the resin followed by eluting the acidic human milk oligosaccharide from the resin using a salt solution this step being conducted between steps (iii) and (iv).

18. The process according to claim 16, subjecting the solution to anion exchange using an anion exchange resin, thereby binding the acidic human milk oligosaccharide to the resin followed by eluting the acidic human milk oligosaccharide from the resin using a salt solution this step being conducted between steps (iv) and (v).

19. The process according to claim 1, subjecting the solution to anion exchange using an anion exchange resin, thereby binding the acidic human milk oligosaccharide to the resin followed by eluting the acidic human milk oligosaccharide from the resin using a salt solution.

* * * * *